(12) United States Patent
Sambongi et al.

(10) Patent No.: US 11,317,014 B2
(45) Date of Patent: Apr. 26, 2022

(54) IMAGE PICKUP APPARATUS, IMAGE CORRECTION METHOD, AND MEDIUM STORING PROGRAM

(71) Applicant: OLYMPUS CORPORATION, Tokyo (JP)

(72) Inventors: Masao Sambongi, Tokyo (JP); Munenori Fukunishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/139,002

(22) Filed: Dec. 31, 2020

(65) Prior Publication Data

US 2021/0127053 A1 Apr. 29, 2021

Related U.S. Application Data

(63) Continuation of application No. PCT/JP2018/026036, filed on Jul. 10, 2018.

(51) Int. Cl.
*H04N 5/232* (2006.01)
*H04N 13/218* (2018.01)

(52) U.S. Cl.
CPC ..... *H04N 5/23212* (2013.01); *H04N 5/23254* (2013.01); *H04N 13/218* (2018.05)

(58) Field of Classification Search
CPC ........... H04N 5/23212; H04N 5/23254; H04N 13/218; H04N 2013/0085; H04N 13/211;

(Continued)

(56) References Cited

U.S. PATENT DOCUMENTS 8,208,549 B2 * 6/2012 Sasai .................... H04N 19/139
382/239
2005/0213663 A1 * 9/2005 Aoyama ................. G06T 7/223
375/240.24

(Continued)

FOREIGN PATENT DOCUMENTS

CN 103339940 A 10/2013
JP 2004-049638 A 2/2004

(Continued)

OTHER PUBLICATIONS

Chinese Office Action dated Oct. 11, 2021 received in 201880094934.2.

(Continued)

*Primary Examiner* — Shahbaz Nazrul
(74) *Attorney, Agent, or Firm* — Scully, Scott, Murphy & Presser, P.C.

(57) ABSTRACT

An image pickup apparatus has a first/second optical system transmitting light through a first/second optical path, the second optical system having parallax with the first optical path; a switcher switching between the first and second optical paths in time series; an image sensor forming a first image and a second image by capturing subject images according to the light transmitted through the first optical path and the second optical path respectively; and a processor processing a signal output from the image sensor, wherein the processor calculates a motion vector in each divided region of a first base image from the first base image and a first reference image captured, interpolates an interpolation motion vector for each pixel of the first base image from the motion vector, and corrects the first base image or the first reference image to form a prediction image of the first image.

13 Claims, 11 Drawing Sheets

(58) Field of Classification Search
CPC ...... H04N 5/225; H04N 5/23267; H04N 7/18; H04N 13/111; H04N 13/133; H04N 13/239; G06T 2207/10012; G06T 2207/20021; G06T 5/003; G06T 5/50; G06T 7/223; A61B 1/00; A61B 1/045; G01B 11/00; G01C 3/06

See application file for complete search history.

(56) References Cited

U.S. PATENT DOCUMENTS

| | | | | |
|---|---|---|---|---|
| 2009/0123083 | A1* | 5/2009 | Kawase | G06T 3/4007 |
| | | | | 382/254 |
| 2011/0063473 | A1* | 3/2011 | Tsunekawa | H04N 9/04515 |
| | | | | 348/222.1 |
| 2011/0122951 | A1* | 5/2011 | Kimura | H04N 7/0132 |
| | | | | 375/240.16 |
| 2016/0057445 | A1* | 2/2016 | Tsubaki | H04N 5/23258 |
| | | | | 382/236 |

FOREIGN PATENT DOCUMENTS

| | | |
|---|---|---|
| JP | 2005-284486 A | 10/2005 |
| JP | 2010-128354 A | 6/2010 |
| JP | 2011205519 A | 10/2011 |
| JP | 2014-126861 A | 7/2014 |
| JP | 2016-218800 A | 12/2016 |
| JP | 2017-038933 A | 2/2017 |

OTHER PUBLICATIONS

International Search Report dated Aug. 28, 2018 issued in PCT/JP2018/026036.

Japanese Notice of Allowance dated Feb. 15, 2022 received in 2020-529878.

* cited by examiner

IMAGE PICKUP APPARATUS, IMAGE CORRECTION METHOD, AND MEDIUM STORING PROGRAM

This application is a continuation application based on a PCT International Application No. PCT/JP2018/026036, filed on Jul. 10, 2018. The content of the PCT International Application is incorporated herein by reference.

TECHNICAL FIELD

The present disclosure relates to a time-division stereo image pickup apparatus, an image correction method, and a computer-readable non-volatile medium storing program.

BACKGROUND ART

In the related art, an image pickup apparatus has been used that has two different optical paths and has a stereo measurement function of measuring the three-dimensional coordinates of a subject and the size of the subject based on the principle of stereo measurement.

For example, as disclosed in Japanese Unexamined Patent Application, First Publication No. 2004-049638, a measurement endoscope apparatus includes two optical systems having parallax. The measurement endoscope apparatus simultaneously picks up an optical image obtained by each optical system. The measurement endoscope apparatus uses the two generated images to calculate the three-dimensional coordinates of a subject and the size of the subject based on the principle of stereo measurement.

A stereo measurement apparatus disclosed in Japanese Unexamined Patent Application, First Publication No. 2010-128354 includes an optical system that forms two images of a subject, which are formed by light that has passed through two different optical paths (referred to as a first optical path and a second optical path) in a common region of an image pickup element. The stereo measurement apparatus includes optical path-switching means for switching the optical path to pick up a subject image formed only by light that has passed through one of the two optical paths.

When measurement of a subject is performed using the stereo measurement apparatus in Japanese Unexamined Patent Application, First Publication No. 2010-128354, an image (referred to as a first image) is generated by performing picking-up based on the first subject image formed by the light that has passed through the first optical path. Then, the optical path is switched, and an image (referred to as a second image) is generated by performing picking-up based on the second subject image formed by the light that has passed through the second optical path. The shape of the subject is measured using the principle of stereo measurement, based on the parallax between the first image and the second image.

In such a time-division stereo image pickup apparatus, the first image and the second image are images picked up at different time points. Thus, a motion shift caused by an image pickup time difference between the first image and the second image may occur. In particular, when a subject is moving fast or when the image pickup apparatus is moving due to camera shake or the like, the motion shift caused by the image pickup time difference between the first image and the second image becomes significant. When the motion shift occurs by the image pickup time difference, stereo measurement may not be performed correctly.

In order to suppress the motion shift caused by the image pickup time difference that occurs in the time-division stereo image pickup apparatus, it is necessary to cancel the image pickup time difference by correcting any one image of the first image and the second image to a prediction image that temporally precedes or follows the first image or the second image.

As a method of correcting an image to a prediction image that temporally precedes or follows the image, there is a method of predicting the motion of the image using a motion vector. For example, an image pickup apparatus disclosed in Japanese Unexamined Patent Application, First Publication No. 2014-126861 detects a motion vector from two images and corrects a reference image to a prediction image without image blur by using the detected motion vector and the like.

When the image picked up by the image pickup apparatus is an image obtained by image pickup of a subject having a large variation in subject distance, the tendency of the change in motion vector often varies depending on the subject distance. In a correction using a motion vector, in which the subject distance is not considered, it is not possible to accurately correct the image to a prediction image which temporally precedes or follows the image.

SUMMARY

According to an aspect of the present disclosure, an image pickup apparatus has a first optical system configured to transmit light through a first optical path; a second optical system configured to transmit light through a second optical path, the second optical system having parallax with the first optical path; a switcher configured to switch between the first optical path and the second optical path in time series; an image sensor configured to generate a first image by capturing a subject image according to the light transmitted through the first optical path and a second image by capturing another subject image according to the light transmitted through the second optical path; and a processor configured to process a signal output from the image sensor. The processor is configured to calculate a motion vector in each divided region of a first base image from the first base image and a first reference image, wherein the first base image and the first reference image are selected from a plurality of the first images, and the first reference image is captured at an image pickup time different from an image pickup time of the first base image, interpolate an interpolation motion vector for each pixel of the first base image from the motion vector according to a brightness value of the divided region in each divided region, and correct the first base image or the first reference image to form a prediction image of the first image using the interpolation motion vector according to the image pickup time point of the second image, wherein the prediction image temporally precedes or follows the first image.

According to another aspect of the present disclosure, an image pickup apparatus has a first optical system configured to transmit light through a first optical path; a second optical system configured to transmit light through a second optical path, the second optical system having parallax with the first optical path; a switcher configured to switch between the first optical path and the second optical path in time series; an image sensor configured to form a first image by capturing a subject image according to the light transmitted through the first optical path and a second image by capturing another subject image according to the light transmitted through the second optical path; and a processor configured to process a signal output from the image sensor. The processor is configured to calculate a motion vector in each divided region of a first base image from the first base image and a first reference image, wherein the first base image and the first reference image are selected from a plurality of the first images, and the first reference image is captured at an image pickup time different from the image pickup time of the first base image, interpolate an interpolation motion vector for each pixel of the first base image from the motion vector according to a contrast value of the divided region in each divided region, and correct the first base image or the first reference image to form a prediction image of the first image using the interpolation motion vector according the image pickup time point of the second image, wherein the prediction image temporally precedes or follows the first image.

According to a further another aspect of the present disclosure, an image correction method has calculating a motion vector in each divided region of a first base image from the first base image and a first reference image, the first reference image being captured at an image pickup time point different from an image pickup time point of the first base image; interpolating an interpolation motion vector for each pixel of the first base image from the motion vector in each divided region, according to a brightness value of the divided region; and correcting the first base image or the first reference image to form a prediction image that of the first image using the interpolation motion vector, wherein the prediction image temporally precedes or follows the first base image or the first reference image.

According to a further another aspect of the present disclosure, a computer-readable non-volatile medium storing a program executed by the computer to perform a method for processing a first image and a second image which are generated by switching between a first optical path and a second optical path having parallax with the first optical path in time series, the first image being generated by capturing a subject image according to light transmitting through the first optical path, and the second image being generated by capturing another subject image according light transmitting through the second optical path, wherein the method has calculating a motion vector in each divided region of a first base image from the first base image and a first reference image, wherein the first base image and the first reference image are selected from a plurality of the first images, and the first reference image is captured at an image pickup time different from an image pickup time of the first base image, interpolating an interpolation motion vector for each pixel of the first base image from the motion vector according to a brightness value of the divided region in each divided region, and correcting the first base image or the first reference image to form a prediction image of the first image using the interpolation motion vector according to the image pickup time point of the second image, wherein the prediction image temporally precedes or follows the first image.

DESCRIPTION OF EMBODIMENTS

First Embodiment

A first embodiment of the present disclosure will be described with reference to FIGS. 1 to 12.

Figure 1:
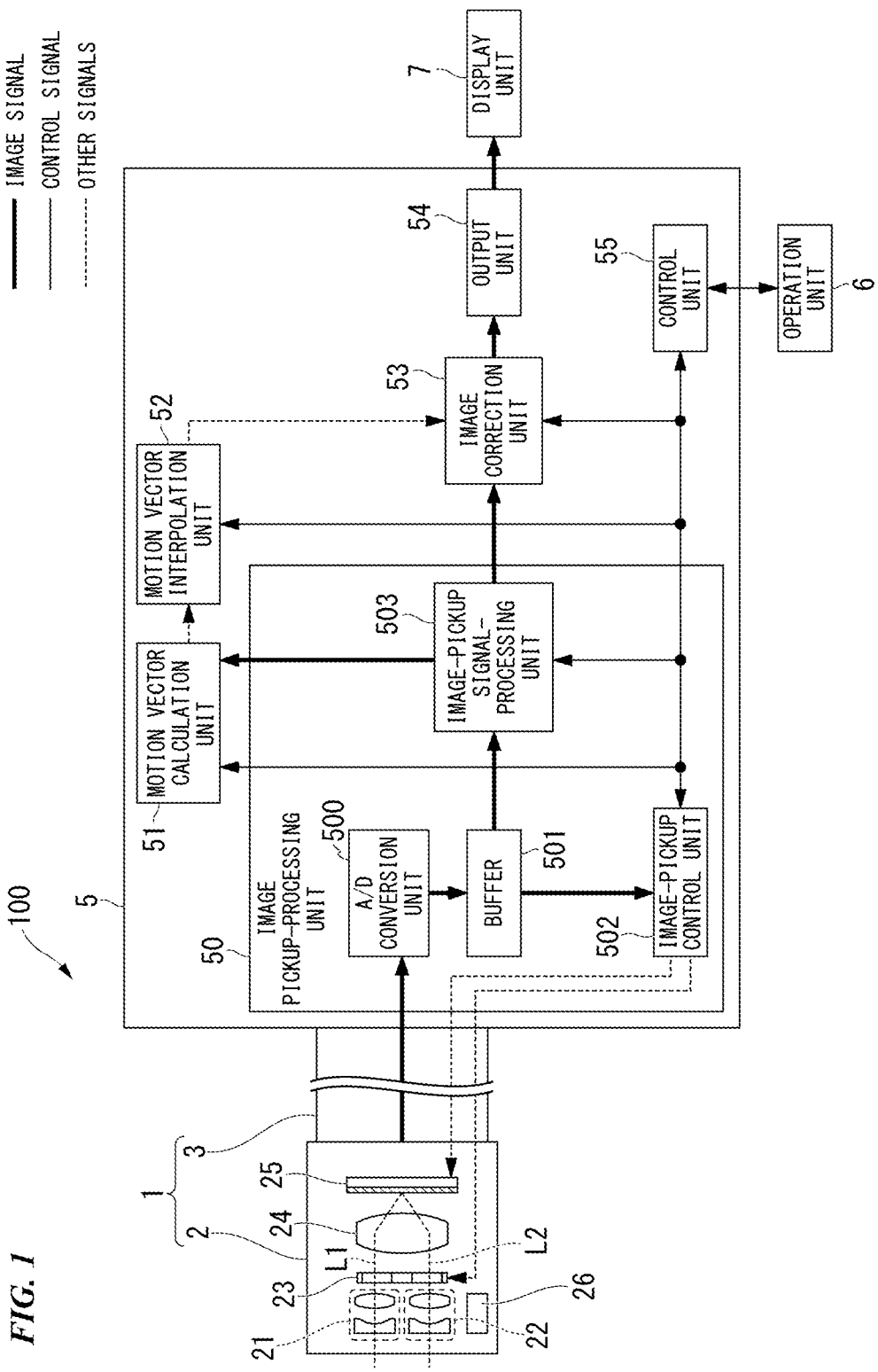
FIG. 1 is a configuration diagram representing an image pickup apparatus according to a first embodiment of the present disclosure.

FIG. 1 is a configuration diagram representing an image pickup apparatus 100 according to a first embodiment of the present disclosure. An example in which the image pickup apparatus 100 is an endoscope apparatus will be described below.

As represented in FIG. 1, the image pickup apparatus 100 includes an insertion unit 1, a control unit 5, an operation unit 6, and a display unit 7.

[Insertion Unit 1]

The insertion unit 1 is inserted into an object to be measured. The insertion unit 1 has a tip portion 2 and an elongated insertion-unit main body 3 that extends in a longitudinal axis direction of the insertion unit 1.

The tip portion 2 is disposed at the tip of the insertion-unit main body 3. The tip portion 2 includes a first optical system 21, a second optical system 22, an optical path-setting unit 23, an imaging optical system 24, an image pickup element (image pickup unit) 25, and an illumination unit 26.

For example, each of the first optical system 21 and the second optical system 22 includes an objective lens obtained by combining a concave lens and a convex lens. The second optical system 22 is disposed to have parallax with the first optical system 21. That is, the first optical system 21 and the second optical system 22 are spaced in a parallax direction. The parallax direction is a direction of a straight line passing through the optical center (principal point) of the first optical system 21 and the optical center (principal point) of the second optical system 22. Light incident to the first optical system 21 passes through a first optical path L1. Light incident to the second optical system 22 passes through a second optical path L2 different from the first optical path L1. The first optical system 21 forms a first image of a subject, and the second optical system 22 forms a second image of the subject.

The optical path-setting unit 23 switches the optical path between the first optical path L1 and the second optical path L2 such that only one of the first image and the second image is formed in an image pickup region of the image pickup element 25. That is, the optical path-setting unit 23 selects either the first optical path L1 or the second optical path L2 as the optical path at the time of image pickup, such that only one of the first image and the second image is formed in the image pickup region of the image pickup element 25. The optical path-setting unit 23 is configured to transmit only the light passing through either the first optical path L1 or the second optical path L2 and to block the light passing through the other.

For example, the optical path-setting unit 23 includes a light-blocking plate inserted on only one of the first optical path L1 and the second optical path L2. When the optical path-setting unit 23 causes the light on the first optical path L1 to be transmitted, the light-blocking plate is inserted on the second optical path L2. Thus, the light on the second optical path L2 is blocked. When the optical path-setting unit 23 causes the light on the second optical path L2 to be transmitted, the light-blocking plate is inserted on the first optical path L1. Thus, the light on the first optical path L1 is blocked. A switching operation of the optical path by the optical path-setting unit 23 is controlled by a control signal from an image-pickup control unit 502 in the control unit 5.

The imaging optical system 24 forms a subject image in the image pickup region of the image pickup element 25, based on either of the light passing through the first optical path L1 and the light passing through the second optical path L2. The subject image is formed in the image pickup region of the image pickup element 25, based on the light that has passed through only the optical path set as the optical path at the time of image pickup, among the first optical path L1 and the second optical path L2.

The image pickup element 25 has the image pickup region in which the first image of a subject, which is formed by light passing through the first optical path L1, and the second image of the subject, which is formed by light passing through the second optical path L2 different from the first optical path L1, are commonly formed. The image pickup element 25 photoelectrically converts the formed subject image to generate an image pickup signal. The image pickup element 25 is, for example, a single-plate charge-coupled device (CCD) image sensor of an RGB primary color system. The image pickup element 25 may be configured by a complementary metal-oxide semiconductor (CMOS). The operation of the image pickup element 25 is controlled by a control signal from the image-pickup control unit 502 in the control unit 5.

The image pickup element 25 picks up the first image through the first optical system 21 at a first image pickup timing. The image pickup element 25 generates an image pickup signal of the "first image" based on the first image formed in the image pickup region. The image pickup element 25 outputs the image pickup signal of the first image to the control unit 5.

The image pickup element 25 picks up the second image through the second optical system 22 at a second image pickup timing different from the first image pickup timing. The image pickup element 25 generates an image pickup signal of the "second image" based on the second image formed in the image pickup region. The image pickup element 25 outputs the image pickup signal of the second image to the control unit 5.

The illumination unit 26 includes a light source that generates illumination light with which a subject is irradiated. For example, the light source is a light-emitting diode (LED). The illumination unit 26 may be disposed in the control unit 5, and the illumination light generated by the illumination unit 26 may be guided to the tip portion 2 by a light guide.

[Control Unit 5]

The control unit (control device) 5 is connected to the insertion unit 1. As represented in FIG. 1, the control unit 5 includes an image pickup-processing unit 50, a motion vector calculation unit 51, a motion vector interpolation unit 52, an image correction unit 53, an output unit 54, and a control unit 55.

The image pickup-processing unit 50 controls the image pickup element 25 and the like of the tip portion 2. The image pickup-processing unit 50 processes the image pickup signal input from the image pickup element 25 to generate an image signal. The image pickup-processing unit includes an A/D conversion unit 500, a buffer 501, the image-pickup control unit 502, and an image-pickup signal-processing unit 503.

The A/D conversion unit 500 converts the image pickup signal of the first image and the image pickup signal of the second image, which are input from the image pickup element 25, into a digital signal and then stores the digital signal in the buffer 501.

The buffer 501 is a volatile storage medium configured by a RAM, a register file, and the like. The buffer 501 can store at least two first images and second images.

The image-pickup control unit 502 controls the switching operation of the optical path by the optical path-setting unit 23 and an operation of the image pickup element 25, based on instructions of the control unit 55. The image-pickup control unit 502 controls an AF motor (not represented) to control the focal lengths of the first optical system 21 and the second optical system 22. The image-pickup control unit 502 controls an electronic shutter speed and the like in order to adjust an incident light quantity by using a brightness level in the image pickup signal and a brightness sensor (not represented).

The image-pickup signal-processing unit 503 reads the image pickup signal in the single plate state, which is stored in the buffer 501 and generates an image signal subjected to white balance processing, image format conversion, interpolation processing, and the like, for example, and to generate an image signal in a RGB three-plate state. The image-pickup signal-processing unit 503 may convert the RGB signal into a brightness color difference signal (YCbCr signal) by calculation represented in Expression 1.

$$\begin{bmatrix} Y(x, y) \\ Cb(x, y) \\ Cr(x, y) \end{bmatrix} = \begin{bmatrix} 0.299 & 0.587 & 0.114 \\ -0.169 & -0.331 & 0.500 \\ 0.500 & -0.419 & -0.081 \end{bmatrix} \begin{bmatrix} R(x, y) \\ G(x, y) \\ B(x, y) \end{bmatrix} \quad \text{Expression 1}$$

Figure 2:
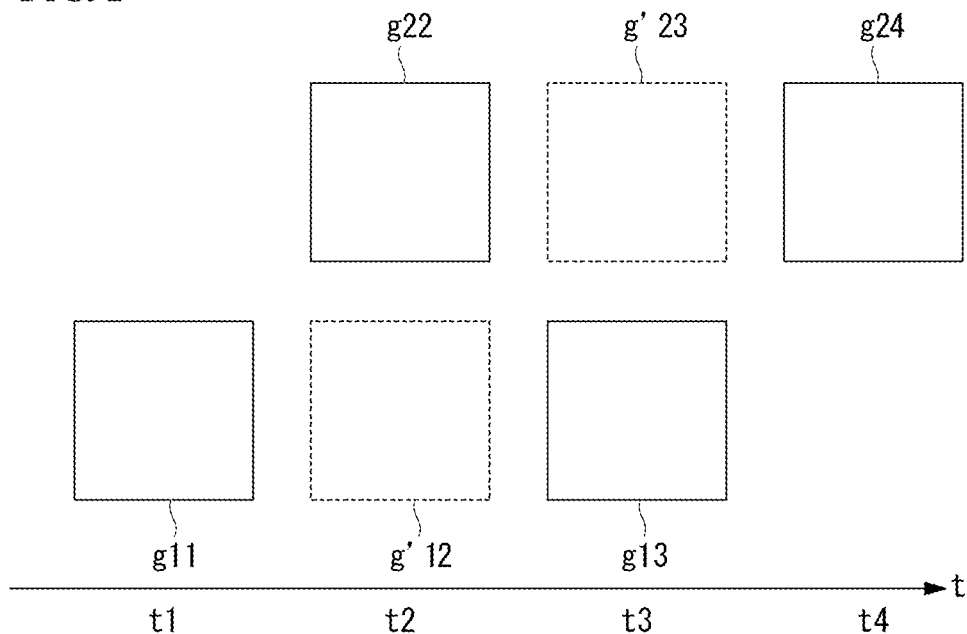
FIG. 2 is a schematic diagram representing an image signal generated by an image pickup-processing unit of the image pickup apparatus in time series.

FIG. 2 is a schematic diagram representing an image signal generated by the image pickup-processing unit 50 in time series.

At a time point t1, the image-pickup control unit 502 controls the optical path-setting unit 23 to cause only light passing through the first optical path L1 to be transmitted. The image pickup element 25 picks up a first image through the first optical system 21, and outputs an image pickup signal of the first image based on the first image formed in the image pickup region to the image pickup-processing unit 50. The image pickup-processing unit 50 converts the image pickup signal of the first image into an image signal g11 of the first image.

Then, at a time point t2, the image-pickup control unit 502 controls the optical path-setting unit 23 to cause only light passing through the second optical path L2 to be transmitted. The image pickup element 25 picks up a second image through the second optical system 22, and outputs an image pickup signal of the second image based on the second image formed in the image pickup region to the image pickup-processing unit 50. The image pickup-processing unit 50 converts the image pickup signal of the second image into an image signal g22 of the second image.

Then, at a time point t3, the image-pickup control unit 502 controls the optical path-setting unit 23 to cause only light passing through the first optical path L1 to be transmitted again. The image pickup element 25 picks up a first image through the first optical system 21, and outputs an image pickup signal of the first image based on the first image formed in the image pickup region to the image pickup-processing unit 50. The image pickup-processing unit 50 converts the image pickup signal of the first image into an image signal g13 of the first image.

As represented in FIG. 2, the image pickup apparatus 100 is a time-division stereo image pickup apparatus that acquires the first image and the second image in a time-division manner. Therefore, the first image g11, the second image g22, and the first image g13 generated by the image pickup-processing unit 50 are image signals obtained by image pickup at different time points.

When stereo measurement is performed based on the parallax between the first image and the second image, the second image g22 and either the first image g11 or the first image g13 are used. However, since the first image (g11 or g13) and the second image (g22) are images picked up at the different time points, a motion shift may occur between the first image and the second image due to the image pickup time difference. In particular, when a subject is moving fast or when the image pickup apparatus is moving due to camera shake or the like, the motion shift caused by the image pickup time difference between the first image and the second image becomes significant. When the motion shift occurs by the image pickup time difference, stereo measurement may not be performed correctly.

The control unit 5 corrects either one of the first images (g11 and g13) into a prediction image g'12 that temporally precedes or follows the first image. As represented in FIG. 2, the prediction image g'12 is a prediction image of the first image at the image pickup time point t2 when the second image g22 is picked up. If the prediction image g'12 and the second image g22 are used in stereo measurement, it is possible to suppress a motion shift caused by an image pickup time difference in stereo measurement. The prediction image g'12 is generated by the motion vector calculation unit 51, the motion vector interpolation unit 52, and the image correction unit 53.

The image pickup-processing unit 50 outputs the first image g11 and the first image g13 to the motion vector calculation unit 51. The image pickup-processing unit 50 outputs the second image g22, the first image g11, and the first image g13 to the image correction unit 53.

Figure 3:
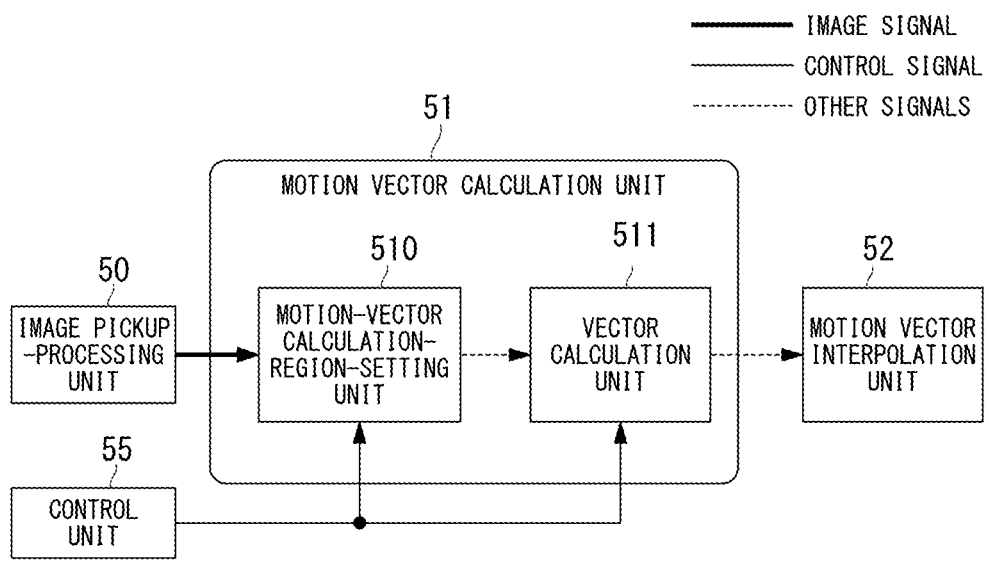
FIG. 3 is a configuration diagram representing a motion vector calculation unit of the image pickup apparatus.

FIG. 3 is a configuration diagram representing the motion vector calculation unit 51.

The motion vector calculation unit 51 includes a motion-vector calculation-region-setting unit 510 and a vector calculation unit 511. The motion vector calculation unit 51 calculates a motion vector from two first images having the same image size (one is referred to as a base frame and the other is referred to as a reference frame).

Two first images (g11 and g13) which are selected from a plurality of first images and have different image pickup time points are input to the motion vector calculation unit 51. The motion vector calculation unit 51 sets the first image g11 as the base frame (first base image) and the first image g13 as the reference frame (first reference image) to calculate the motion vector from the first image g11 to the first image g13 (motion vector calculation step).

Figure 4:
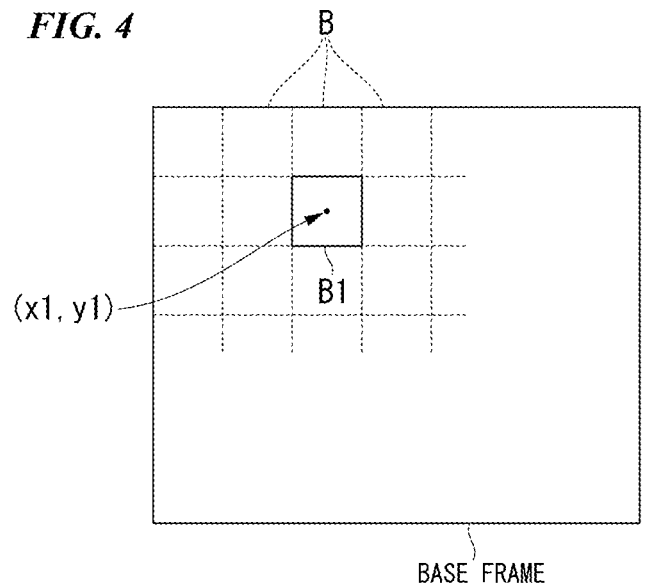
FIG. 4 is a schematic diagram representing motion vector calculation region setting of the image pickup apparatus.
Figure 5:
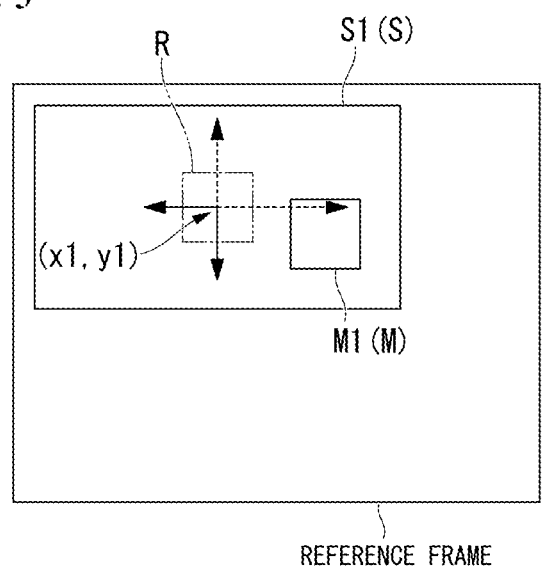
FIG. 5 is a schematic diagram representing the motion vector calculation region setting of the image pickup apparatus.

FIGS. 4 and 5 are schematic diagrams representing a motion vector calculation region setting. FIG. 4 represents a base frame, and FIG. 5 represents a reference frame.

The motion vector calculation unit 51 detects a region (matching block M) similar to a specific region (base block B) in the base frame from a specific region (search block S) in the reference frame. Then, the motion vector calculation unit calculates the motion vector based on the positional relationship between the base block B and the matching block M. The base block B and the matching block M have the same region size.

The base block (divided region) B is a region obtained by dividing the base frame, for example, into regions of 5 pixels in a horizontal direction and 5 pixels in a vertical direction (referred to as "5×5" below). Base points (for example, center point, pixel at the upper left end, and gravity center) of the base block B are arranged at predetermined pixel intervals in the horizontal direction and the vertical direction.

The search block S is a region larger than the base block B, for example, a "9×9" region, and is used as a search region for the matching block M.

In the following description, XY coordinates are used to describe the position of the pixel of an image. The horizontal direction is set to an X-axis direction, the vertical direction is set to a Y-axis direction, and the upper left is set to the origin. The XY coordinates are expressed as (X,Y)=(0,0).

The motion-vector calculation-region-setting unit 510 sets a search block S as a search target, for each base block B. The search block S is set such that the base point coordinates of the base block B are included in the coordinate range of the search block S. For example, as represented in FIGS. 4 and 5, when the center coordinates of the base block B1 are (x1, y1), the search block S1 is set to be an image having (x1, y1) as the center.

The motion-vector calculation-region-setting unit 510 selects image data of the base block B and the search block S paired with the base block B from the base frame and the reference frame input from the image-pickup signal-processing unit 503. Then, the motion-vector calculation-region-setting unit outputs the selected image data to the vector calculation unit 511.

Figure 6:
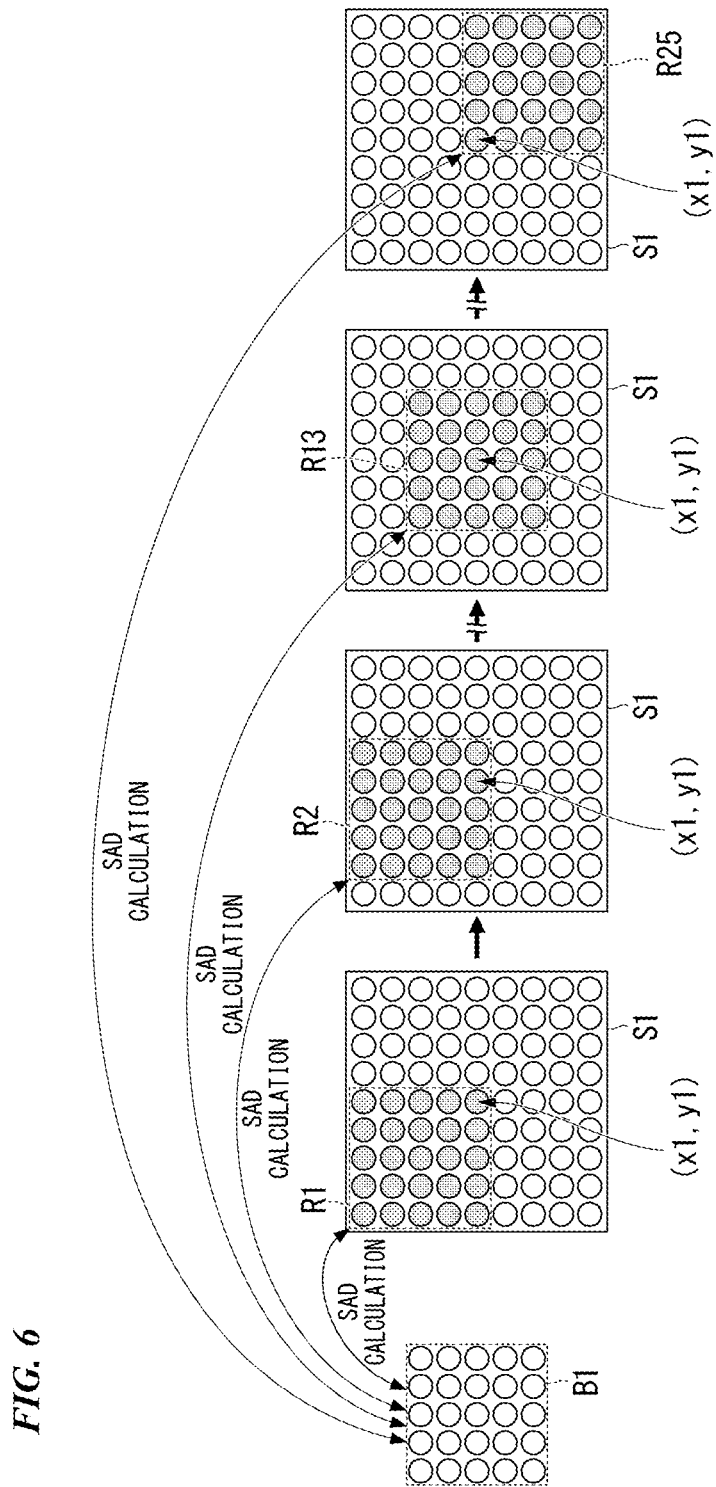
FIG. 6 is a schematic diagram representing motion vector calculation of the image pickup apparatus.

FIG. 6 is a schematic diagram representing motion vector calculation.

As represented in FIG. 6, the vector calculation unit 511 sets reference blocks (R1-R25) having a region size which is equal to the region size of a base block B1, by using the search block S1. Then, the vector calculation unit calculates the similarity between the base block B1 and each of the reference blocks (R1-R25). As represented in FIG. 6, the reference blocks (R1 to R25) refer to a plurality of regions that differ by one pixel in the X-direction or the Y-direction in the region of the search block S1.

For example, index values such as sum of absolute differences (SAD), sum of squared differences (SSD), normalized cross correlation (NCC), and zero means normalized cross correlation (ZNCC) may be used as the similarity.

The vector calculation unit 511 may set a reference block R13 as a start point to obtain the similarity by sequentially calculating the similarity to each of the reference blocks which are vertically and horizontally adjacent to the base block. The reference block R13 has center coordinates of (x1, y1) which are the center coordinates of the base block B1. The vector calculation unit 511 may obtain the similarity by calculating the similarity of a plurality of reference blocks set in the search block S1 in parallel.

When the calculation of the similarity between the base block B1 and all the reference blocks (R1-R25) is completed, the vector calculation unit 511 sets the reference block having the highest similarity, as a matching block M1. The vector calculation unit 511 determines the difference of the coordinates of the base point of the base block B1 from the coordinates of a predetermined base point (for example, center point, pixel at the upper left end, and gravity center) of the selected matching block M1, as the "motion vector". When none of the similarities between the base block B1 and the reference blocks (R1 to R25) reach the predetermined similarity, a detection result of the motion vector is "undetected".

Then, the motion-vector calculation-region-setting unit 510 and the vector calculation unit 511 sequentially detect motion vectors of other base blocks B in the base frame being processed, and detect the motion vectors for all the base blocks B.

The vector calculation unit 511 outputs the motion vector detected for the base block B to the motion vector interpolation unit 52. Regarding the base block B for which the motion vector has not been detected, the vector calculation unit outputs a motion "vector-undetected flag" indicating that the motion vector has not been detected.

Figure 7:
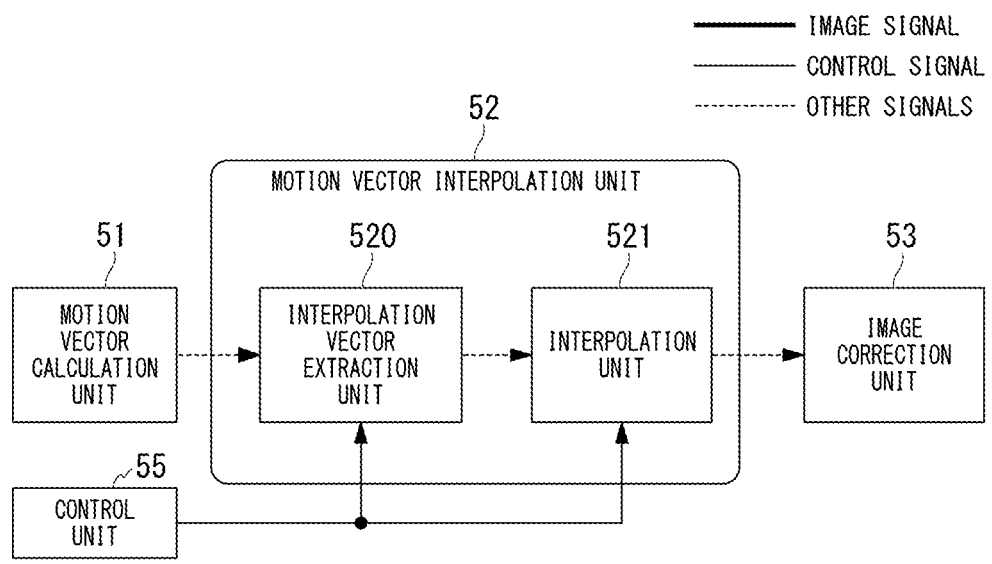
FIG. 7 is a configuration diagram representing a motion vector interpolation unit of the image pickup apparatus.

FIG. 7 is a configuration diagram representing the motion vector interpolation unit 52.

The motion vector interpolation unit 52 includes an interpolation vector extraction unit 520 and an interpolation unit 521. The motion vector interpolation unit 52 generates a motion vector (interpolation motion vector) of each pixel from the motion vector obtained for each base block B by the motion vector calculation unit 51, by interpolation (motion vector interpolation step).

The interpolation vector extraction unit 520 extracts a motion vector used for interpolation from the motion vector of each base block B, which is transmitted from the motion vector calculation unit 51. The interpolation vector extraction unit 520 extracts four motion vectors by the known four-neighbor selection method. The extracted motion vectors are motion vectors of the base block B (i) which is close to target coordinates generated by interpolation of the motion vector and (ii) in which the motion vector has been detected.

Figure 8:
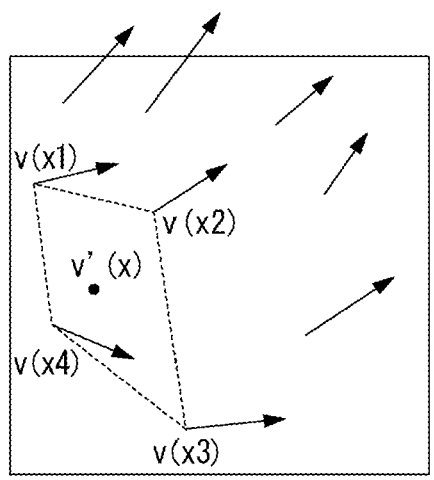
FIG. 8 is a schematic diagram representing motion vector interpolation performed by the image pickup apparatus.

FIG. 8 is a schematic diagram representing motion vector interpolation.

For example, as represented in FIG. 8, the interpolation vector extraction unit 520 extracts motion vectors $v(x_1)$ to $v(x_4)$ being four neighbors close to the target coordinates $x(x, y)$ generated by the interpolation of the motion vector. The interpolation vector extraction unit 520 outputs the extracted motion vectors $v(x_1)$ to $v(x_4)$ to the interpolation unit 521.

The interpolation unit 521 uses the extracted motion vectors $v(x_1)$ to $v(x_4)$ and calculation represented by Expression 2 to calculate a motion vector v' (x) in coordinates x(x, y) by four-neighbor interpolation.

$$v'(x) = \frac{\Sigma_j \; w_j v(x_j)}{\Sigma_j \; w_j} \qquad \text{Expression 2}$$

wj in Expression 2 is a weight by a plane distance in an image space as in Expression 3, for example. Here, the plane distance is a distance between the coordinates x(x, y) and the base point xj of the base block B corresponding to the extracted motion vector.

$$w_j = w_x(x, x_j) \qquad \text{Expression 3}$$

Wx(x, xj) in Expression 3 can be obtained by Expression 4, for example. Here, σx indicates the variance in the Gaussian distribution in the image space.

$$w_x(x, x_j) = \exp\left(-\frac{|x - x_j|^2}{2\sigma_x^2}\right) \qquad \text{Expression 4}$$

Wx(x, xj) is not limited to the Gaussian function shown in Expression 4, and may be the weight shown in Expression 5. In Expression 5, a indicates any constant.

$$w_x(x, x_j) = \begin{cases} -\frac{1}{a}|x - x_j| + 1, & 0 \le |x - x_j| \le a \\ 0, & |x - x_j| > a \end{cases} \qquad \text{Expression 5}$$

Wx(x, xj) may be the weight shown in Expression 6.

$$w_x(x, x_j) = \frac{1}{|x - x_j| + 1} \qquad \text{Expression 6}$$

When the difference in plane distance between the coordinates x and the extracted motion vectors $v(x_1)$ to $v(x_4)$ is large, the interpolation unit 521 decreases the weight. When the difference in plane distance between the coordinates x and the extracted motion vectors $v(x_1)$ to $v(x_4)$ is small, the interpolation unit 521 increases the weight.

Figure 9:
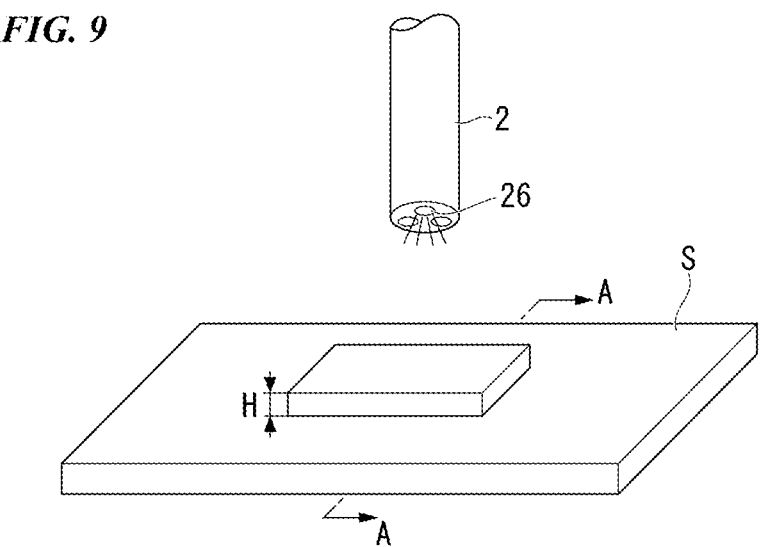
FIG. 9 is a diagram representing a form in which the image pickup apparatus picks up an image of a subject.
Figure 10:
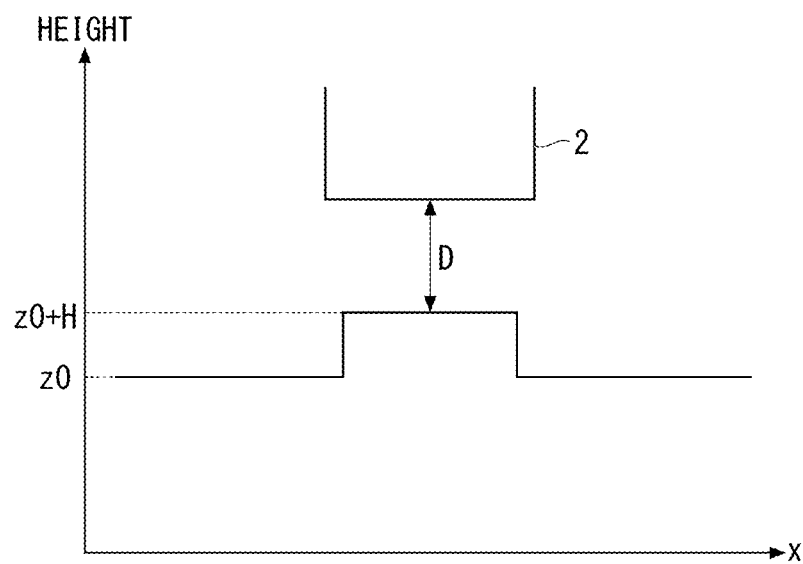
FIG. 10 is a sectional view taken along line A-A of the subject represented in FIG. 9.

FIG. 9 is a diagram representing a form in which the image pickup apparatus 100 picks up an image of a subject S. The subject S represented in FIG. 9 has a variation in distance (subject distance D) from the tip portion 2 of the image pickup apparatus 100. FIG. 10 is a sectional view taken along line A-A of the subject represented in FIG. 9. A horizontal axis of a graph indicates the coordinates in the x-axis horizontal to the A-A section. As represented in FIG. 10, the subject distance D is different between a portion at which the height of the subject S is $Z_0$ and a portion at which the height of the subject S is $Z_0+H$.

When the image pickup apparatus 100 picks up an image of the subject S having a large variation in subject distance D, a motion vector detected from the first image g11 and the first image g13 may have a tendency of change in the motion vector that often varies depending on the subject distance D. For example, the motion vector of a pixel corresponding to an image obtained by image pickup of a portion having a short subject distance D changes significantly. The motion vector of a pixel corresponding to an image obtained by image pickup of a portion having a long subject distance D changes smaller. Therefore, when only the weight by the plane distance of the image space, which is shown in Expression 3, is used in the interpolation of the motion vector v' (x), it is not possible to perform correct generation of the motion vector v' (x) by interpolation.

Figure 11:
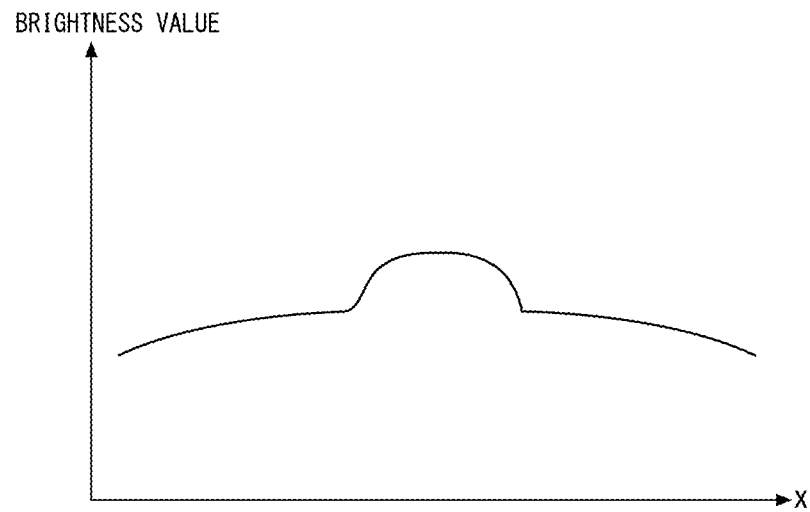
FIG. 11 is a graph representing a brightness value of a surface of an A-A section of the subject represented in FIG. 9.

FIG. 11 is a graph representing a brightness value of the surface of the A-A section of the subject represented in FIG. 9. A horizontal axis of a graph indicates the coordinates in the x-axis horizontal to the A-A section.

When the reflectance of the subject is substantially uniform, the brightness distribution depends on the subject distance. The subject is uniformly irradiated with illumination light from the illumination unit 26 in the tip portion 2 of the image pickup apparatus 100. Therefore, it can be roughly determined that the portion having the high brightness value in the subject has a short subject distance D, and the portion having the low brightness value in the subject has a long subject distance D. The interpolation unit 521 may use the brightness value of the subject in the calculation of wj in Expression 2.

The interpolation unit 521 uses, as wj in Expression 2, the product of the weight based on the plane distance in the image space and the weight based on a brightness difference, as in Expression 7. Here, the brightness difference is a brightness difference (gradient) between a brightness value d at the coordinates x (x, y) and a brightness value dj of the base point of the base block B corresponding to the extracted motion vector. Here, the brightness value is a Y signal or a G signal.

$$w_j = w_x(x, x_j) w_d(d, d_j) \qquad \text{Expression 7}$$

Wd(d,dj) in Expression 7 can be obtained by Expression 8, for example. Here, σd indicates the variance in the Gaussian distribution in the brightness signal.

$$w_d(d, d_j) = \exp\left(-\frac{|d - d_j|^2}{2\sigma_d^2}\right) \qquad \text{Expression 8}$$

Wd(d,dj) is not limited to the Gaussian function shown in Expression 8, and may be the weight shown in Expression 9. In Expression 9, b indicates any constant.

$$w_d(d, d_j) = \begin{cases} -\frac{1}{b}|d - d_j| + 1, & 0 \le |d - d_j| \le b \\ 0, & |d - d_j| > b \end{cases} \qquad \text{Expression 9}$$

Wd(d,dj) may be the weight shown in Expression 10.

$$w_d(d, d_j) = \frac{1}{|d - d_j| + 1} \qquad \text{Expression 10}$$

When the brightness difference is large, the interpolation unit 521 determines that a depth difference between the coordinate x and the extracted motion vectors $v(x_1)$ to $v(x_4)$ is large, and decreases the weight. When the brightness difference is small, the interpolation unit 521 determines that the depth difference between the coordinate x and the extracted motion vectors $v(x_1)$ to $v(x_4)$ is small, and increases the weight. The interpolation unit 521 can correct the motion vector in consideration of the subject distance D by such weighting.

The interpolation unit 521 outputs the motion vector v' (x) of each pixel, which is calculated by the interpolation to the image correction unit 53.

The interpolation unit 521 may use a contrast value instead of the brightness value. In this case, Wd(d,dj) can be obtained, for example, as shown in Expression 11.

$$w_d(d, d_j) = \begin{cases} \dfrac{d_j}{d}, & d > d_j \\ \dfrac{d}{d_j}, & d \le d_j \\ 0, & d \text{ or } d_j = 0 \end{cases} \qquad \text{Expression 11}$$

The image correction unit 53 corrects either one of the first images (g11 or g13) to the prediction image g'12 that temporally precedes or follows the first image, based on the calculated motion vector v' (x) of each pixel (image correction step). In the present embodiment, the first image g11 is corrected to the prediction image g'12. The motion vector v" (x) from the first image g11 to the prediction image g'12 can be obtained by Expression 12.

$$v''(x) = \frac{t_2 - t_1}{t_3 - t_1} v'(x) \qquad \text{Expression 12}$$

When an interval between the time point t1 and the time point t2 is equal to an interval between time point t2 and the time point t3, the magnitude of the motion vector v" (x) is half of the magnitude of the motion vector v' (x).

The image correction unit 53 can generate the prediction image g' 12 by a known method by applying the motion vector v" (x) to all the pixels in the first image g11. The image correction unit 53 outputs the first images (g11 and g13), the second image g22, and the generated prediction image g'12 to the output unit 54.

The output unit 54 generates a display image by selecting or combining the first images (g11 and g13), the second image g22, and the generated prediction image g' 12, and transmits the display image to the display unit 7 at a predetermined transmission timing.

When the output unit 54 creates a display image in which the second image g22 and the prediction image g' 12 are arranged side by side, a user can observe a stereo image at the image pickup time point t2, on the display unit 7.

The control unit 55 controls the tip portion 2, the operation unit 6, and the display unit 7 in addition to the image pickup-processing unit 50, the motion vector calculation unit 51, the motion vector interpolation unit 52, the image correction unit 53, and the output unit 54. The control unit 55 sets operation parameters for the above components, based on an input from the operation unit.

Figure 12:
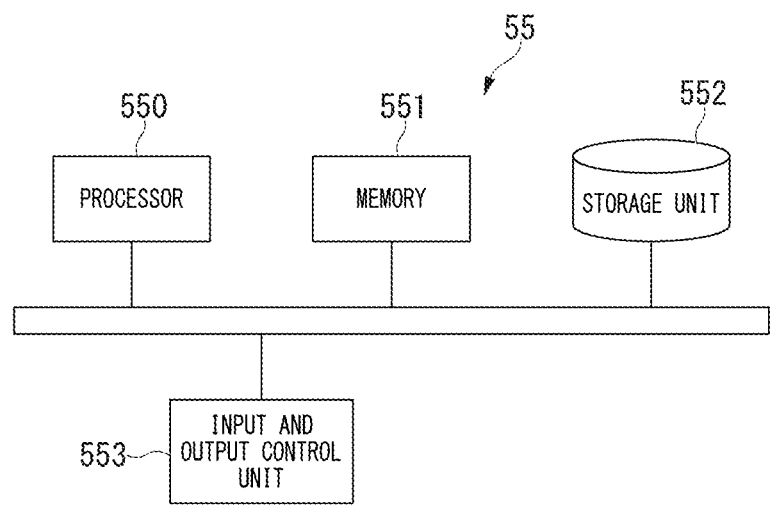
FIG. 12 is a configuration diagram representing a control unit of the image pickup apparatus.

FIG. 12 is a configuration diagram representing the control unit 55.

As represented in FIG. 12, the control unit 55 is a program-executable processing device (computer) including a processor 550, a program-readable memory 551, a storage unit 552, and an input and output control unit 553. The processor 550 executes a program provided for the control unit 55, so as to realize the function of the control unit 55.

At least some function of the control unit 55 may be configured by a dedicated logic circuit or the like.

For example, the processor 550 is a CPU, a digital signal processor (DSP), a graphics processing unit (GPU), or a combination thereof.

The input and output control unit 553 performs an internal communication in the control unit 5 and communications for operation control with the tip portion 2, the operation unit 6, and the display unit 7.

The storage unit 552 is a non-volatile recording medium that stores the above-described program and necessary data. The storage unit 552 is configured by, for example, a ROM or a flash memory. A program recorded in the storage unit 552 is read into the memory 551 and executed by the processor 550.

The above-described program may be provided, for example, by a "computer-readable recording medium" such as a flash memory. The above-described program may be transmitted to the image pickup apparatus 100 from a computer including a storage device or the like in which the program is stored, via a transmission medium or by a transmission wave in the transmission medium. The "transmission medium" for transmitting the program is a medium having a function of transmitting information, such as a network (communication network) (for example, Internet) and a communication circuit line (communication line) (for example, telephone line). The above-described program may be a difference file (difference program) that enables realization of the function of the control unit 55 in combination with a program causing the function of the control unit to be already recorded in the control unit 55.

Similar to the control unit 55, the image pickup-processing unit 50, the motion vector calculation unit 51, the motion vector interpolation unit 52, the image correction unit 53, and the output unit 54 may be configured by a program-executable processing device (computer) including a processor and the like, by a dedicated electronic circuit (logic circuit or the like) or a combination thereof.

Each of the image pickup-processing unit 50, the motion vector calculation unit 51, the motion vector interpolation unit 52, the image correction unit 53, the output unit 54, and the control unit 55 may be configured by a separate processing device or electronic circuit. Alternatively, at least some of the above components may be configured by a common processing device or electronic circuit.

[Operation Unit 6]

The operation unit 6 is a user interface that receives instructions from the user. The user operates the operation unit 6 to input instructions necessary for controlling various operations of the entire image pickup apparatus 100. The operation unit 6 outputs a signal indicating the instruction received from the user to the control unit 55. For example, the operation unit 6 is at least one of a shutter button, a setting button, a setting switch, a key, a mouse, a joystick, a touch pad, a trackball, and a touch panel.

[Display Unit 7]

The display unit 7 displays the display image output by the output unit 54. The display unit 7 also displays the operation control content. For example, the operation control content is displayed as a menu. For example, the display unit 7 is at least one of a liquid crystal display and an organic electroluminescence (EL) display. The display unit 7 may be a touch panel display. In this case, the operation unit 6 and the display unit 7 are integrated.

The operation unit 6 and the display unit 7 are not essential in the image pickup apparatus 100.

[Operation of Image Pickup Apparatus 100]

Next, the operation of the image pickup apparatus 100 according to the first embodiment will be described.

Firstly, the user moves the tip portion 2 to a position at which an image of the subject is enabled to be picked up. Then, the user operates the operation unit 6 to start image pickup with the image pickup apparatus 100.

The image pickup apparatus 100 picks up the first image g11 at the time point t1 as illustrated in FIG. 2. Then, at the time point t2, the image pickup apparatus 100 controls the optical path-setting unit 23 to switch the optical path, and then picks up the second image g22. Then, at the time point t3, the image pickup apparatus 100 controls the optical path-setting unit 23 to switch the optical path, and then picks up the first image g13. Then, at a time point t4, the image pickup apparatus 100 controls the optical path-setting unit 23 to switch the optical path, and then picks up a second image g24.

The image pickup apparatus 100 completes the image pickup of the first image g13, and then generates the prediction image g'12 from the first image g11 and the first image g13. As represented in FIG. 2, the prediction image g'12 is a prediction image of the first image at the time point t2 when the second image g22 is picked up. The generated prediction image g'12 is output from the output unit 54 to the display unit 7.

The image pickup apparatus 100 completes the image pickup of the second image g24, and then generates a prediction image g'23 from the second image g22 and the second image g24. As represented in FIG. 2, the prediction image g'23 is a prediction image of the second image at the time point t3 when the first image g13 is picked up. The generated prediction image g'23 is output from the output unit 54 to the display unit 7.

The image pickup apparatus 100 alternately repeats the generation of the prediction image of the first image and the generation of the prediction image of the second image, until an operation stop instruction is given from the operation unit 6.

According to the image pickup apparatus 100 in the present embodiment, it is possible to correct even an image obtained by image pickup of a subject having a large variation in subject distance, to a prediction image that temporally precedes or follows the image and to provide a stereo image (first image and second image) picked up at the same time point.

According to the image pickup apparatus 100 of the present embodiment, the motion vector v' (x) is used for generating the prediction image, and the motion vector v' (x) of each image is obtained from the motion vector v(x) obtained for each base block B, by interpolation. Therefore, it is possible to obtain motion vectors v' (x) of all pixels at a high speed. In the interpolation of the motion vector v' (x), the brightness value is used as a weight in the interpolation calculation. Therefore, it is possible to correct the motion vector in consideration of the subject distance D.

As described above, the first embodiment of the present disclosure has been described in detail with reference to the drawings, but the specific configuration is not limited to this embodiment, and includes design changes and the like without departing from the scope of the present disclosure. The constituent elements described in the above-described first embodiment and modification examples described below can be appropriately configured by combinations thereof.

Modification Example 1

At least some functions of the image pickup apparatus 100 according to the above embodiment may be realized by a computer. In this case, the functions may be realized in a manner such that a program for realizing the function is recorded in a computer-readable recording medium, and the program recorded in this recording medium is read and executed by a computer system. It is assumed that the "computer system" described here includes an OS and hardware such as peripheral devices. The "computer-readable recording medium" refers to a portable medium such as a flexible disk, a magneto-optical disk, a ROM, a CD-ROM, or a storage device such as a hard disk mounted in a computer system. Further, the "computer-readable recording medium" may refer to a medium that dynamically holds a program for a short time, for example, a communication line when the program is transmitted via a network such as the Internet or a communication circuit line such as a telephone line. In this case, the "computer-readable recording medium" may include a medium that holds the program for a predetermined time, for example, a volatile memory in a computer system as a server or a client.

Figure 13:
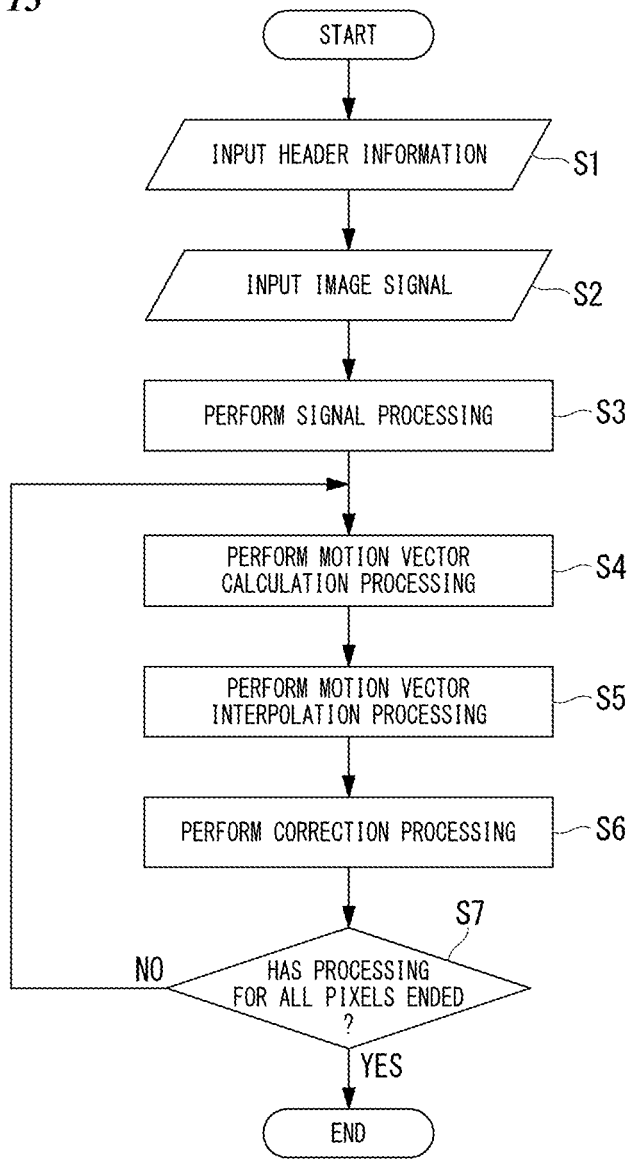
FIG. 13 is a flowchart representing a program operated by an external computer system as a modification example of the image pickup apparatus.

For example, the image pickup element 25 outputs the image pickup signal as Raw data, and ISO sensitivity information, the image signal size, and the like as header information, to an external computer system. The external computer system executes a program to realize the remaining functions of the image pickup apparatus 100. FIG. 13 is a flowchart representing the program operated by the external computer system.

As represented in FIG. 13, the computer system reads header information in Step S1, and then reads time-series image pickup signals in Step S2.

In Step S3, the computer system performs signal processing corresponding to the processing of the image-pickup signal-processing unit 503.

In Step S4, the computer system performs processing corresponding to the motion vector calculation unit 51, to calculate a motion vector.

In Step S5, the computer system performs processing corresponding to the motion vector interpolation unit 52, to interpolate a motion vector of each pixel.

In Step S6, the computer system performs processing corresponding to the image correction unit 53, to correct an image signal.

In Step S7, the computer system determines whether the processing of the image (frame) scheduled to be processed has ended. When the processing for all the images (all frames) has ended, the computer system ends the processing.

Modification Example 2

In the above embodiment, the four-neighbor interpolation is used in the interpolation of the motion vector v' (x), but the interpolation method of the motion vector is not limited to the above embodiment. The motion vector interpolation may be nearest neighbor interpolation that selects the nearest one point, or the interpolation may be performed by extracting the nearest eight points.

Modification Example 3

In the above embodiment, the prediction image g'12 generated by the interpolation is the prediction image at the image pickup time point t2 between the image pickup time point t1 of the first image g11 and the image pickup time point t3 of the first image g13. The form of the prediction image is not limited to the above embodiment. A prediction image at a time before the image pickup time point t1 or at a time after the image pickup time point t3 may be generated by the interpolation based on the motion vector v' (x) detected based on the first image g11 and the first image g13.

Modification Example 4

In the above embodiment, a functional expression such as the Gaussian function is used for calculating the weight in interpolation of the motion vector, but the weight calculation method is not limited to the above embodiment. The weight in the interpolation of the motion vector may be calculated by a look-up table determined by an empirical rule or the like. The look-up table uses the plane distance, the brightness value, and the like as an input and outputs the weight.

Second Embodiment

A second embodiment of the present disclosure will be described with reference to FIGS. 14 to 16. In the following description, components which are common with the components already described are denoted by the same reference signs, and repetitive description thereof will be omitted. The present embodiment is different from the first embodiment in that the control unit includes a distance-measuring unit.

Figure 14:
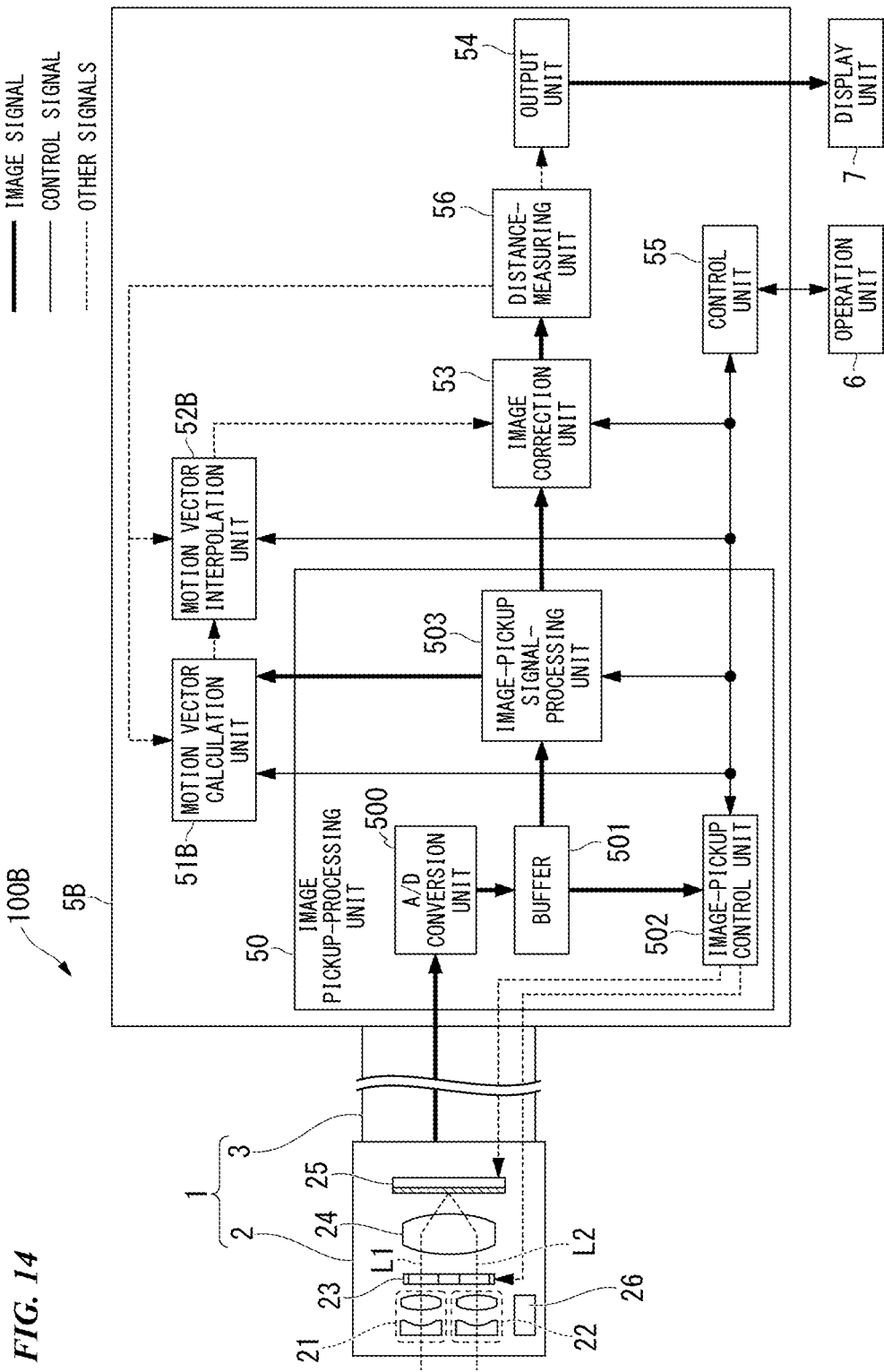
FIG. 14 is a configuration diagram representing an image pickup apparatus according to a second embodiment of the present disclosure.

FIG. 14 is a configuration diagram representing an image pickup apparatus 100B according to the present embodiment.

As represented in FIG. 14, the image pickup apparatus 100B includes an insertion unit 1, a control unit 5B, an operation unit 6, and a display unit 7.

As represented in FIG. 14, the control unit 5B includes a distance-measuring unit 56 in addition to an image pickup-processing unit 50, a motion vector calculation unit 51B, a motion vector interpolation unit 52B, an image correction unit 53, an output unit 54, and a control unit 55.

The distance-measuring unit 56 receives the second image g22 output by the image correction unit 53 and the prediction image g'12 generated by the image correction unit 53. The distance-measuring unit 56 measures the subject distance D from the tip portion 2 to the subject for each pixel by a known stereo measurement method. The subject distance is measured from the second image g22 picked up at the time point t2 and the prediction image g'12 of the first image at the time point t2. The distance-measuring unit 56 outputs the measured subject distance D of each pixel to the motion vector calculation unit 51B and the motion vector interpolation unit 52B.

The motion vector calculation unit 51B includes a motion-vector calculation-region-setting unit 510B and a vector calculation unit 511. After processing the first image g11 and the first image g13, the motion vector calculation unit 51B calculates a motion vector for each base block B from the second image g22 and the second image g24. Here, the motion vector calculation unit 51B is different from the motion vector calculation unit 51 in that the size of the region of the base frame B is not uniform but variable.

Figure 15:
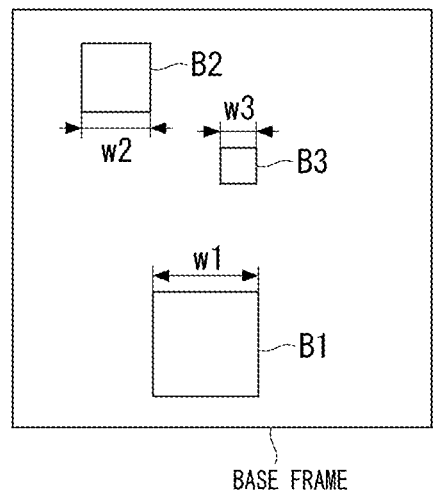
FIG. 15 is a schematic diagram representing motion vector calculation region setting of the image pickup apparatus.
Figure 16:
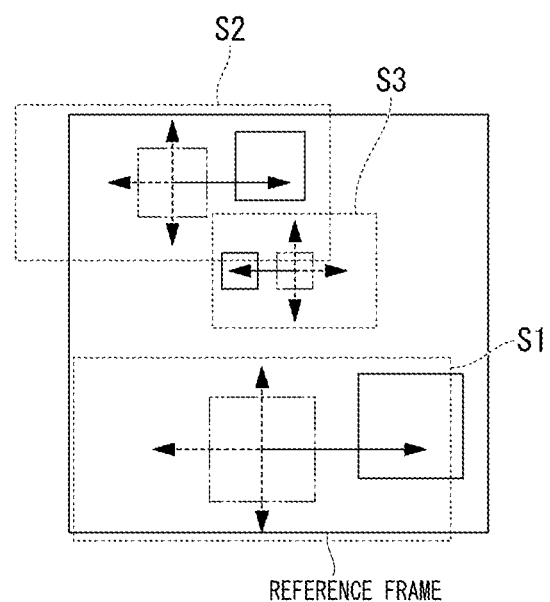
FIG. 16 is a schematic diagram representing the motion vector calculation region setting of the image pickup apparatus.

FIGS. 15 and 16 are schematic diagrams representing motion vector calculation region setting. FIG. 15 represents a base frame, and FIG. 16 represents a reference frame.

The motion-vector calculation-region-setting unit 510B uses the subject distance D of each pixel, which is input from the distance-measuring unit 56, to determine the size of the region of the base block B at base points aligned in the horizontal and vertical directions at predetermined pixel intervals.

For example, when the subject distance D in the pixel of the base point of the base block B is short, the motion-vector calculation-region-setting unit 510B sets the size of the region of the base block B to be large like a region B1 in FIG. 15.

When the subject distance D in the pixel at the base point is short, the pixel of the base point indicates an image obtained by image pickup of a subject close to the tip portion 2. Thus, a probability indicating a tendency that the motion vector of a pixel in the vicinity of the base point is the same as the motion vector of the pixel at the base point is high. Therefore, efficiency of motion vector detection processing is increased by increasing the size of the region of the base block B.

When the subject distance D in the pixel at the base point of the base block B is long, the motion-vector calculation-region-setting unit 510B sets the region of the base block B to have a small size, like a region B3 in FIG. 15.

When the subject distance D in the pixel at the base point is long, the pixel of the base point indicates an image obtained by image pickup of a subject far from the tip portion 2. Thus, a probability indicating a tendency that the motion vector of a pixel in the vicinity of the base point is the same as the motion vector of the pixel at the base point is low. Therefore, accuracy of motion vector detection processing is increased by decreasing the size of the region of the base block B.

As represented in FIG. 16, the motion-vector calculation-region-setting unit 510B sets a search block S to be searched for each base block B, based on the size of the region of the base block B.

As represented in FIG. 16, a search block S1 having a large region is set for a base block B1 having a large region. A search block S3 having a small region is set for a base block B3 having a small region.

The motion vector interpolation unit 52B generates a motion vector of each pixel by the interpolation from the motion vector obtained based on the second image g22 and the second image g24 by the motion vector calculation unit 51B. In this interpolation, the subject distance D of each pixel, which is measured from the stored second image g22 and prediction image g'12 of the first image, is used.

For example, wj in Expression 2 is calculated by a function shown in Expression 13, for example. Here, z is the subject distance D at the coordinate x (x, y), and zj is the subject distance D at the base point of the base block B corresponding to the extracted motion vector.

$$w_z(z, z_j) = \exp\left(-\frac{|z - z_j|^2}{2\sigma_z^2}\right)$$ Expression 13

Wz (z, zj) in Expression 13 can be obtained by Expression 14, for example. Here, σz represents the variance in the Gaussian distribution in the image space.

$$w_j = w_x(x, x_j) w_d(d, d_j) w_z(z, z_j)$$ Expression 14

Although all Wx(x, xj), Wd(d, dj), and Wz(z, zj) are used as the weight shown in Expression 13, any one or any two of the above weights may be selected and used.

The motion vector interpolation unit 52B decreases the weight when the subject distance D is large. The motion vector interpolation unit 52B increases the weight when the subject distance D is small. With such weighting, the motion vector interpolation unit 52B can correct the motion vector in consideration of the subject distance D stereo-measured in practice.

According to the image pickup apparatus 100B in the present embodiment, similar to the image pickup apparatus 100 according to the first embodiment, it is possible to correct even an image obtained by image pickup of a subject having a large variation in subject distance, to a prediction image that temporally precedes or follows the image and to provide a stereo image (first image and second image) picked up at the same time point. It is possible to perform accurate stereo measurement using the stereo image.

According to the image pickup apparatus 100B of the present embodiment, the stereo measurement result is fed back to determine the region sizes of the base block B and the search block S corresponding to the subject distance D. As a result, the image pickup apparatus 100B has higher efficiency of motion vector detection processing and higher motion vector detection accuracy than the image pickup apparatus 100.

According to the image pickup apparatus 100B of the present embodiment, it is possible to perform accurate motion vector interpolation corresponding to the subject distance D, by feeding back the stereo measurement result.

As described above, the second embodiment of the present disclosure has been described in detail with reference to the drawings, but the specific configuration is not limited to this embodiment, and includes design changes and the like without departing from the scope of the present disclosure. The constituent elements described in the above-described second embodiment and modification examples described below can be appropriately configured by combinations thereof.

Modification Example 5

Figure 17:
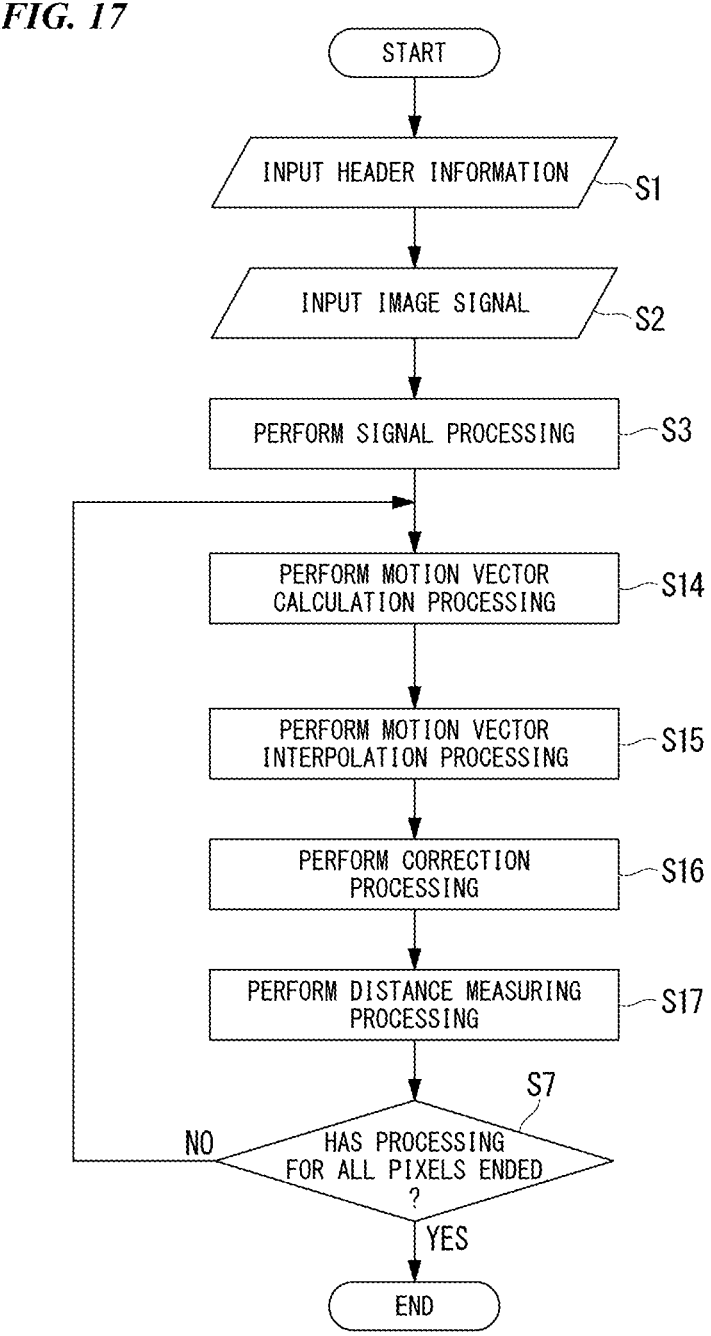
FIG. 17 is a flowchart representing a program operated by an external computer system as a modification example of the image pickup apparatus.

At least some functions of the image pickup apparatus 100B according to the above embodiment may be realized by a computer. For example, the image pickup element 25 outputs the image pickup signal as Raw data, and ISO sensitivity information, the image signal size, and the like as header information, to an external computer system. The external computer system executes a program to realize the remaining functions of the image pickup apparatus 100. FIG. 17 is a flowchart representing the program operated by the external computer system.

Steps S1 to S3 and S7 are the same as Steps S1 to S3 and S7 described in the Modification Example 1 of the first embodiment.

As represented in FIG. 17, the computer system performs processing corresponding to the motion vector calculation unit 51B in Step S14, to calculate a motion vector from the first images (g11 and g13).

In Step S15, the computer system performs processing corresponding to the motion vector interpolation unit 52B, to interpolate a motion vector of each pixel based on the first images (g11 and g13).

In Step S16, the computer system performs processing corresponding to the image correction unit 53, to generate the prediction image g'12 based on the first image g11 and the first image g13.

In Step S17, the computer system performs processing corresponding to the distance-measuring unit 56, to measure the subject distance D for each pixel from the tip portion 2 to the subject from the second image g22 picked up at the time point t2 and the prediction image g'12 of the first image at the time point t2. The measured subject distance D is stored.

In Step S7, the computer system determines whether the processing of the image (frame) scheduled to be processed has ended. When the processing for all the images (all frames) has ended, the computer system ends the processing. When processing the next frame, the computer system executes Step S14 again.

In Step S14, the computer system performs processing corresponding to the motion vector calculation unit 51B, to calculate a motion vector from the second image (g22 and g24). The subject distance D stored in the previous Step S17 is used to calculate the motion vector.

In Step S15, the computer system performs processing corresponding to the motion vector interpolation unit 52B, to interpolate a motion vector of each pixel, based on the second image (g22 and g24). The subject distance D stored in the previous Step S17 is used to interpolate the motion vector.

In Step S16, the computer system performs processing corresponding to the image correction unit 53, to generate the prediction image g' 23 based on the second image g22 and the second image g24.

In Step S17, the computer system performs processing corresponding to the distance-measuring unit 56, to measure the subject distance D for each pixel from the tip portion 2 to the subject based on the first image g13 picked up at the time point t3 and the prediction image g' 23 of the second image at the time point t3. The measured subject distance D is stored.

In Step S7, the computer system determines whether the processing for all the target pixel of the image signal has ended. When the processing for all the target pixels has been completed, the computer system ends the processing.

Several embodiments and modification examples of the present disclosure have been described above, however, technical scope of the present disclosure is not limited to the embodiment and the application examples. Additions, omissions, substitutions and other changes in the structure are possible without departing from the spirit of the present disclosure. The present disclosure is not limited to the above-described embodiments and is limited only by the accompanying claims.

What is claimed is:

1. An image pickup apparatus, comprising:
a first optical system configured to transmit light through a first optical path;
a second optical system configured to transmit light through a second optical path, the second optical system having parallax with the first optical path;
a switcher configured to switch between the first optical path and the second optical path in time series;
an image sensor configured to generate a first image by capturing a subject image according to the light transmitted through the first optical path and a second image by capturing another subject image according to the light transmitted through the second optical path; and
a processor configured to process a signal output from the image sensor,
wherein the processor is configured to:
calculate a motion vector in each divided region of a first base image from the first base image and a first reference image, wherein the first base image and the first reference image are selected from a plurality of the first images, and the first reference image is captured at an image pickup time different from an image pickup time of the first base image,
interpolate an interpolation motion vector for each pixel of the first base image from the motion vector according to a brightness value of the divided region in each divided region, and
correct the first base image or the first reference image to form a prediction image of the first image using the interpolation motion vector according to the image pickup time point of the second image, wherein the prediction image temporally precedes or follows the first image.

2. The image pickup apparatus according to claim 1, wherein the processor is configured to correct the first base image or the first reference image to form the prediction image of the first image at the same pickup time point as the image pickup time point of the second image.

3. The image pickup apparatus according to claim 1, wherein the processor is configured to use a gradient of the brightness value of the divided region as a weight in interpolation of the interpolation motion vector.

4. The image pickup apparatus according to claim 3, wherein the processor is configured to decrease the weight as the gradient of the brightness value increases, and increases the weight as the gradient of the brightness value decreases.

5. The image pickup apparatus according to claim 1, wherein the processor is configured to use a contrast value of the divided region as a weight in interpolation of the interpolation motion vector, instead of the brightness value.

6. The image pickup apparatus according to claim 1, wherein the processor is configured to further perform stereo measurement using the second image and the prediction image of the first image.

7. The image pickup apparatus according to claim 6, wherein the processor is configured to use a subject distance measured during the stereo measurement as a weight in interpolation of the interpolation motion vector.

8. The image pickup apparatus according to claim 7, wherein the processor is configured to decrease the weight as the subject distance increases, and increases the weight as the subject distance decreases.

9. The image pickup apparatus according to claim 7, wherein the processor is configured to set a size of the divided region based on the subject distance.

10. The image pickup apparatus according to claim 9, wherein the processor is configured to set the size of the divided region to become larger as the subject distance decreases, and to become smaller as the subject distance increases.

11. An image pickup apparatus, comprising:
a first optical system configured to transmit light through a first optical path;
a second optical system configured to transmit light through a second optical path, the second optical system having parallax with the first optical path;
a switcher configured to switch between the first optical path and the second optical path in time series;
an image sensor configured to form a first image by capturing a subject image according to the light transmitted through the first optical path and a second image by capturing another subject image according to the light transmitted through the second optical path; and
a processor configured to process a signal output from the image sensor,
wherein the processor is configured to:
calculate a motion vector in each divided region of a first base image from the first base image and a first reference image, wherein the first base image and the first reference image are selected from a plurality of the first images, and the first reference image is captured at an image pickup time different from the image pickup time of the first base image, interpolate an interpolation motion vector for each pixel of the first base image from the motion vector according to a contrast value of the divided region in each divided region, and correct the first base image or the first reference image to form a prediction image of the first image using the interpolation motion vector according the image pickup time point of the second image, wherein the prediction image temporally precedes or follows the first image.

12. An image correction method, comprising:

calculating a motion vector in each divided region of a first base image from the first base image and a first reference image, the first reference image being captured at an image pickup time point different from an image pickup time point of the first base image;

interpolating an interpolation motion vector for each pixel of the first base image from the motion vector in each divided region, according to a brightness value of the divided region; and correcting the first base image or the first reference image to form a prediction image that of the first image using the interpolation motion vector, wherein the prediction image temporally precedes or follows the first base image or the first reference image.

13. A computer-readable non-volatile medium storing a program executed by the computer to perform a method for processing a first image and a second image which are generated by switching between a first optical path and a second optical path having parallax with the first optical path in time series, the first image being generated by capturing a subject image according to light transmitting through the first optical path, and the second image being generated by capturing another subject image according light transmitting through the second optical path, the method comprises:

calculating a motion vector in each divided region of a first base image from the first base image and a first reference image, wherein the first base image and the first reference image are selected from a plurality of the first images, and the first reference image is captured at an image pickup time different from an image pickup time of the first base image, interpolating an interpolation motion vector for each pixel of the first base image from the motion vector according to a brightness value of the divided region in each divided region, and correcting the first base image or the first reference image to form a prediction image of the first image using the interpolation motion vector according to the image pickup time point of the second image, wherein the prediction image temporally precedes or follows the first image.

* * * * *